United States Patent [19]

Corbett

[11] 4,055,896
[45] Nov. 1, 1977

[54] OCCLUSAL PROGRAMMING UNIT

[76] Inventor: Andrew Neville Corbett, 345 Stirling Highway, Claremont, Australia, 6010

[21] Appl. No.: 674,092

[22] Filed: Apr. 6, 1976

[51] Int. Cl.$^2$ .............................................. A61C 9/00
[52] U.S. Cl. ........................................................ 32/19
[58] Field of Search ..................................... 32/32, 19

[56] References Cited

U.S. PATENT DOCUMENTS

| 1,799,528 | 4/1931 | Phillips | 32/19 |
| 3,482,312 | 12/1969 | Smith | 32/19 |

*Primary Examiner*—Robert Peshock
*Attorney, Agent, or Firm*—Haseltine, Lake & Waters

[57] ABSTRACT

An occlusal programming unit for obtaining an intra-oral recording of a patient's jaw movements comprising a pair of substantially triangular plates formed from a rigid synthetic resin, the peripheral area of each plate being so dimensioned in cross section so that the plate can be readily trimmed to fit the individual shape of the patient's dental arch; the inner face of each plate being provided with a series of grooves or channels leading to the periphery of the plate, in each of which a model locating pin may be located and fixed; model reference pins removably positioned in sockets in the outer faces of the plates; a plurality of scribing pins each adapted to be positioned in one of a series of holes on the inner surface of one plate so that they project towards the inner surface of the other plate; and a spring to hold the plates apart intra-orally, the ends of the springs being located in one of each pair of sockets provided on the inner surfaces of the plates.

5 Claims, 1 Drawing Figure

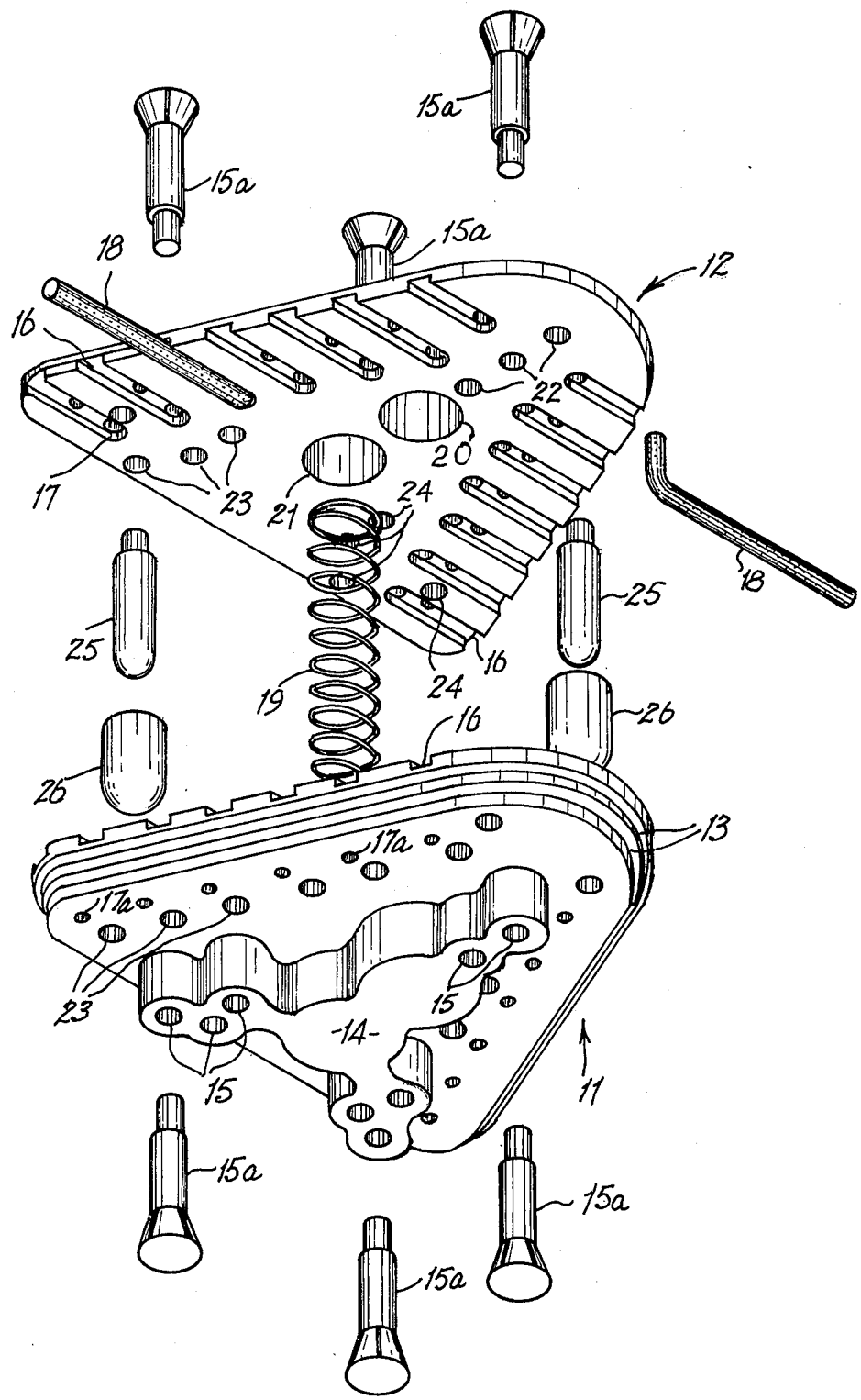

OCCLUSAL PROGRAMMING UNIT

This invention relates to an occlusal programming unit for obtaining an intraoral recording of a patient's jaw movements.

One technique to allow for intraoral programming of the movement of the mandible with respect to the maxilla involves the use of metal plates with various holes and a spring. One such device is described in U.S. Pat. No. 3,482,312. The use of these devices has been limited by the fact that they cater primarily for normal relationships of the mandible to the maxilla anteroposteriorally and vertically. Because of their metal construction, they are unsuitable for custom grinding to the varied requirements of individual cases, and hence, must be supplied in various sizes for both maxilla and mandible at relatively high cost. These plates are also designed in such a way that they are not interchangeable for use in either dental arch.

The object of the present invention is:
(a) To provide a means for registering the complex movements of the mandible with reference to the maxilla, in a moulded plastic intraorally, so that mandibular movements may be reproduced outside the mouth without the use of pantographic equipment and sophisticated fully adjustable articulators.
b. To provide a means for making intra-oral gothic arch tracings for use in preliminary diagnosis prior to oral restorative procedures.

In one form, the invention resides in an occlusal programming unit for obtaining an intraoral recording of a patients jaw movements comprising a pair of substantially triangular plates formed from a rigid synthetic resin; the peripheral area of each plate being so dimensioned in cross section so that the plate can be readily trimmed to fit the individual requirements of the patient's dental arch; the inner face of each plate being provided with a series of grooves or channels leading to the periphery of the plate, in each of which a model locating pin may be located and fixed; model reference pins removably positioned in sockets in the outer faces of the plates; a plurality of scribing pins each adapted to be positioned in one of a series of holes on the inner surface of one plate so that they project towards the inner surface of the other plate; and a spring to hold the plates apart intraorally the ends of the spring being located in one of each pair of sockets provided on the inner surfaces of the plates.

The invention will be better understood by reference to the following description of one specific embodiment thereof shown in the accompanying drawing which is a perspective exploded view.

As shown in the drawing each plate 11 and 12 is moulded from a suitable synthetic resin using suitable techniques such as injection moulding and is substantially triangular in shape with rounded corners so that it will fit in a patients mouth with relative ease. The outer periphery of each plate is of relatively thin cross section compared to the remainder of the plate by the provision of a series of steps 13, so that it can be readily trimmed with cutting instruments or other tools normally available in a dental surgery to fit casts of the patients jaws which have been mounted by means of a centric relation record in a simple hinged articulator. The outer face of each plate is provided with a reinforcing rib 14, the outer end of each rib being provided with one or more sockets 15 into which the end of one of a series of model reference pins 15a can be removably fitted. A series of inwardly directed retention grooves 16 are provided at spaced intervals around the periphery of each plate along the individual sides thereof on the inner surface, each groove being provided with a series of retention holes 17. Before fitting the plates 12, 13 to the models of the patients teeth the surfaces of preparation on the teeth together with other areas likely to be chosen as tooth reference areas are covered with soft wax or similar material so that during subsequent reference operations the models are not abraded. The plates after trimming to the individual requirements of each dental arch are then located on the model using model reference pins 15a which are located in the selected holes 15 at one end and cemented into holes prepared in the model of the patients teeth at the other end with self curing resin or other suitable substance. The plates are positioned between the casts of the patients teeth in such a way that when cemented to each model by the supporting model reference pins the tracing pins with the attached spacer do not touch the inner surface of the opposing plate 12 or 13. The plates 12, 13 are then referenced to the teeth on the model using knurled indexing rods 18 which fit into one of the retention grooves 16 and associated retention hole 17 and are locked in position by a piece of acrylic resin or the like (not shown) which may anchor in another of the retention holes 17(a) to prevent any movement of the indexing rods.

Prior to fixing the indexing rods in position on the plates a small amount of wax is removed at the proposed point planned as a tooth reference stop and the tooth reference rod is seated into self curing resin within the groove 16 and hole 17 and at the point of contact of the reference rod with the tooth. At the time of applying the resin a small amount is allowed to flow around the tracing pins to lock them against rotation. After the indexing rods have been fixed to the plates on the study models the programming plates with the attached indexing rods are transferred to the mouth from the articulator after removal of the plates 12, 13 from the model reference pins 15a to the same position in the mouth as already planned on the patients casts. The plates are held apart by a short coil spring 19 the ends of which are adapted to be located in one of a pair of sockets 20 and 21 provided in the inner surfaces of the plates. The sockets 20 and 21 provide for forward or rearward variation of the position of the spring 19 depending on the skeletal relationship of the jaws. A series of holes 22, 23 and 24 are provided on each plate, each hole being adapted to removably receive one end of a scribing pin 25, the other end of which may be fitted with a spacer 26 if required. As the scribing pins 25 have already been positioned in one of the plates 12, 13 on the simple hinge articulator, after checking that the tooth reference rods "clear" each other in trial movements of the mandible, a small amount of ZnO Eugenol Paste or similar material is placed over the tooth indexing rods and the plates are positioned intraorally with spring to provide separation. A lump of recording material such as acrylic resin is positioned on the other plate opposite each of the scribing pins and as it sets is held in place anteriorally by holes 22, grooves 16 and retention holes 17 and posteriorally by the retention grooves 16 retention holes 17 and holes 21, 23 whilst the patient moves his jaws. With removal of the spacer over the tracing pin a small gap of constant width is established between the tracing pin and the moulded pattern which enables the moulding process to be repeated to obtain greater accuracy by placing a further amount of plastic within the moulded fossae and repeating the same jaw movements as used to obtain the primary fossae mouldings. When the resin sets a record of the patients jaw movements is left in the moulded plastic material.

In order to make a gothic arch tracing of the jaw movement a small tracing plate having projections on one face thereof is fitted to the inner surface of the plate 12 with the projections located in sockets 20 and 21. A tracing pin is then fitted to the inner surface of the plate 11 so that it projects with its outer end bearing against the tracing plate.

The patient is instructed to open his mouth whereupon the spring and plates are removed. The plates are then trimmed of excess periphery outside the moulding on one plate and outside the tracing pins on the other plate including cutting off the tooth indexing rods.

The plates are then fully seated onto the model reference pins with the models themselves removed from the articulator.

The models are removed from the articulator; the teeth having preparations are prepared for removal from the model and the plates are seated into the same position they occupied prior to their removal for the clinical procedures onto the model reference pins.

The tooth preparations are now ready for waxing; the occlusal programmer facilitates the reproducing of the actual jaw movements described in the mouth.

The tracing pins and spring may be positioned to suit various relationships of the jaws without the need to vary the position of the plate itself.

The model reference pins may be positioned to suit the width of the patient's dental arch.

Since the plates are custom grindable the tooth reference pins may be positioned into custom prepared grooves and holes where necessary without the need to use existing grooves and retention holes.

The occlusal programming unit of the present invention provides the following advantages:

a. greater reduction in cost per unit;
b. ready adaptability to individual arch measurements with trimming of the plates and hence a greater number of cases may be treated simultaneously at a far lower cost and without waiting for the correct size metal plate to be ready for reuse;
c. less confusion in the lay-out of retention and other holes and general pattern design;
d. adjustable inter-maxillary spring position producing more consistently accurate results.
e. greater adaptability of tracing pins to various inter-maxillary jaw relationships antero-posteriorally;
f. greater ease of removal from prepared die casts since no screws are required for this purpose;
g. more positive retention of pattern material by virtue of greater number and design of retention grooves and holes;
h. less potential for rotation of teeth indexing wires since they lie within a channel filled with resin and not just a small square hole;
i. the recording plates are identical for use on either the maxilla or mandible;
j. the stylus length is readily adjustable to suit varying lengths of teeth and intermaxillary space.
k. the use of a cap on the stylus allows for a "wash" of acrylic resin to effect the final accurate moulding pattern without the need to grind the moulded pattern for this purpose;
l. the stylus is not a stress bearing member;
m. the plates may be used with its added components of a tracing stylus and table for intra-oral gothic arch tracings once indexed to the patients teeth.
n. by virtue of its disposability and cost the pattern is ideal for storage as a patients record.
o. prior to the intra-oral moulding process it is important to have support under the area opposing the tracing pin since otherwise the "lump" of acrylin placed opposite the tracing pin spills over the edge of the plate.

The claims defining the invention are as follows:

1. An occlusal programming unit for the intraoral recording of jaw movements comprising:
    a. a pair of generally triangular plates of rigid synthetic resin adapted to be positioned adjacent the upper and lower jaws of a patient's mouth during intraoral recording of the patient's jaw movements, each of said plates having a periphery of sufficient dimensions to permit peripheral trimming thereof to the shape of and dimensions of the patient's dental arches, and each of said plates having a first surface adapted to face towards the other plate intraorally and a second surface adapted to face away from the other plate intraorally, each of said first surfaces being provided with a series of grooves extending inwardly from the periphery of the respective plate for receiving locating rods, a series of holes for receiving scribing pins, and a pair of sockets for receiving an end of a spring, and each of said second surfaces being provided with a series of openings for receiving model reference pins;
    b. model reference pins for locating said plates on models of the patient's jaws, said model reference pins being removably receivable in said openings, to permit said plates to be withdrawn from the models and placed in the patient's mouth;
    c. locating rods for identifying the positions of reference teeth when said plates are on the model of the patient's jaws, to thereby aid in positioning said plates in the patient's mouth, said locating rods being receivable in said grooves and being adapted to be fixed in the latter so as to permit identification of the positions of the reference teeth intraorally;
    d. scribing pins for tracing the movements of the patient's jaws intraorally, said scribing pins being receivable in said holes and being dimensioned so as to project outwardly of said holes in said plates towards the respective other plate; and
    e. a spring for holding said plates apart intraorally, said spring having a pair of spaced ends each of which is received in a socket of a different one of said plates intraorally.

2. An occlusal programming unit as claimed in claim 1 wherein the periphery of each plate is stepped.

3. An occlusal programming unit as claimed in claim 1, wherein each of said grooves is provided with a series of retention holes for fixing said locating rods in said grooves.

4. An occlusal programming unit as claimed in claim 1, wherein the outer end of each of said scribing pins is provided with a spacer, each of said spacers being removable so as to permit a gap to be formed between said scribing pins and an intraoral recording of the patient's jaw movements made while said spacers are mounted on said scribing pins whereby the intraoral recording process may be repeated prior to removing said plates from the patient's mouth so as to obtain increased accuracy.

5. An occlusal programming unit as claimed in claim 4 wherein the sides of the scribing pin are parallel and adjustable in length and wherein the removeable spacer may fit the pin at the adjusted length.

* * * * *